(12) United States Patent
Duncan et al.

(10) Patent No.: US 7,448,271 B2
(45) Date of Patent: Nov. 11, 2008

(54) INSPECTION SYSTEM AND ASSOCIATED METHOD

(75) Inventors: Michael J. Duncan, Sumner, WA (US); Mark A. Lee, Kent, WA (US); Fred D. Young, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 524 days.

(21) Appl. No.: 11/205,964

(22) Filed: Aug. 17, 2005

(65) Prior Publication Data

US 2007/0039390 A1 Feb. 22, 2007

(51) Int. Cl.
  *G01N 29/265* (2006.01)
  *G01N 29/06* (2006.01)
(52) U.S. Cl. ....................................................... 73/634
(58) Field of Classification Search .................... 73/632, 73/633, 634, 583, 602
  See application file for complete search history.

(56) References Cited

U.S. PATENT DOCUMENTS

| | | | | |
|---|---|---|---|---|
| 4,014,207 A * | 3/1977 | Meyer et al. .................. 73/621 |
| 4,170,145 A | 10/1979 | Kennedy et al. |
| 4,209,022 A * | 6/1980 | Dory .......................... 600/457 |
| 4,306,458 A * | 12/1981 | Weyns et al. .................. 73/621 |
| 4,381,787 A * | 5/1983 | Hottinger .................... 600/443 |
| 4,474,064 A | 10/1984 | Naruse et al. |
| 4,492,119 A * | 1/1985 | Dulapa et al. ................. 73/621 |
| 6,377,865 B1 * | 4/2002 | Edelsbrunner et al. ........ 700/98 |
| 6,522,906 B1 * | 2/2003 | Salisbury et al. ............ 600/407 |
| 6,722,202 B1 | 4/2004 | Kennedy et al. |
| 2004/0145754 A1 * | 7/2004 | Dickinson et al. ........... 356/614 |
| 2005/0015209 A1 * | 1/2005 | Wuebker ..................... 702/38 |

FOREIGN PATENT DOCUMENTS

| | | |
|---|---|---|
| DE | 28 31 395 | 1/1980 |
| DE | 28 52 560 | 1/1980 |
| DE | 32 24 037 | 12/1983 |
| FR | 2 490 484 | 3/1982 |
| GB | 2 111 682 | 7/1983 |
| JP | 60082829 A * | 5/1985 |
| JP | 08015478 A * | 1/1996 |
| WO | WO 2004/074808 * | 9/2004 |

OTHER PUBLICATIONS

Invitation to Pay Additional Fees mailed Nov. 28, 2006 for PCT/US2006/030045 (Filed Aug. 2, 2006).

* cited by examiner

*Primary Examiner*—Hezron E. Williams
*Assistant Examiner*—Rose M Miller
(74) *Attorney, Agent, or Firm*—Alston & Bird LLP

(57) ABSTRACT

A system and method for inspecting a structure are provided. The system includes at least one non-destructive inspection ("NDI") sensor capable of acquiring data indicative of at least a portion of the structure, and at least one positional sensor for acquiring positional data of the NDI sensor. The system also includes a mechanism operable to trigger the NDI sensor and/or the positional sensor to acquire data such that data indicative of the structure and the positional data are acquired at approximately the same time. The system further includes a movable arm carrying the sensors and movably attached to a base. The system includes a data acquisition system capable of communicating with the sensors such that the data acquisition system generates information indicative of at least a portion of the structure based on the data acquired by the sensors.

15 Claims, 4 Drawing Sheets

INSPECTION SYSTEM AND ASSOCIATED METHOD

BACKGROUND OF THE INVENTION

1) Field of the Invention

The present invention relates to non-destructive inspection and, more particularly, to non-destructive inspection of a structure for defects using an inspection system in conjunction with a data acquisition system.

2) Description of Related Art

Non-destructive inspection ("NDI") of structures involves thoroughly examining a structure without harming the structure or requiring significant disassembly. Non-destructive inspection is typically preferred to avoid the schedule, labor, and costs associated with removal of a part for inspection, as well as avoidance of the potential for damaging the structure. NDI is advantageous for many applications in which a thorough inspection of the exterior and/or interior of a structure is required. For example, NDI is commonly used in the aircraft industry to inspect aircraft structures for any type of internal or external damage to or defects (flaws) in the structure. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Among the structures that are routinely non-destructively tested are composite structures, such as composite sandwich structures and other adhesive bonded panels and assemblies and structures with contoured surfaces. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform NDI. One or more sensors may move over the portion of the structure to be examined, and receive data regarding the structure. For example, a pulse-echo (PE), through-transmission (TT), or shear-wave sensor may be used to obtain ultrasonic data, such as for thickness gauging, detection of laminar defects and porosity, and/or crack detection in the structure. Resonance, pulse-echo, or mechanical impedance sensors are typically used to provide indications of voids or porosity, such as in adhesive bondlines of the structure. High resolution inspection of aircraft structure is commonly performed using ultrasonic testing (UT) to provide a plan view image of the part or structure under inspection. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and/or detectors.

NDI may be performed manually by technicians who move an appropriate sensor over the structure. Manual scanning requires a trained technician to move the sensor over all portions of the structure needing inspection. Manual scanning typically involves the technician repeatedly moving a sensor side-to-side in one direction while simultaneously indexing the sensor in another direction. In addition, because sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have also been developed. For example, the Mobile Automated Scanner (MAUS®) system is a mobile scanning system that employs a fixed frame and one or more automated scanning heads typically adapted for ultrasonic inspection. A MAUS system may be used with pulse-echo, shear-wave, and through-transmission sensors. The fixed frame may be attached to a surface of a structure to be inspected by vacuum suction cups, magnets, or like affixation methods. Smaller MAUS systems may be portable units manually moved over the surface of a structure by a technician.

Furthermore, automated inspection systems have been implemented. For example, the Automated Ultrasonic Scanning System (AUSS®) system is a complex mechanical scanning system that may employ through-transmission ultrasonic inspection. An AUSS system can also perform pulse-echo inspections and simultaneous dual frequency inspections. The AUSS system has robotically controlled probe arms that may be positioned, for example, for TTU inspection proximate the opposed surfaces of the structure undergoing inspection with one probe arm moving an ultrasonic transmitter along one surface of the structure, and the other probe arm correspondingly moving an ultrasonic receiver along the opposed surface of the structure. To maintain the ultrasonic transmitter and receiver in proper alignment and spacing with one another and with the structure undergoing inspection, a conventional automated inspection system may have a complex positioning system that provides motion control in numerous axes, such as the AUSS-X system which has motion control in ten axes.

Multi-axis robots have been used sparingly in NDI because of their inability to determine the exact position of the NDI sensor (i.e., tooltip) in real-time. Robot controllers typically give CPU priority to servo controllers to ensure that the robot closely follows its programmed path. However, robot vendors are reluctant to provide position feedback because their product is intended to be programmed where to go but does not report where it is located. Furthermore, robots that have been utilized for NDI are unable to obtain a three-dimensional position of the sensor as the sensor acquires data. Moreover, because the frequency at which the sensor is able to acquire data has been limited, the resolution and accuracy of the NDI sensor has also been limited.

It would therefore be advantageous to provide an inspection system that is capable of acquiring both NDI data and positional data associated with the NDI data. It would also be advantageous to acquire NDI data more precisely and rapidly as the position of the sensor is measured. It would be further advantageous to provide an inspection system that is capable of inspecting structures having complex shapes.

BRIEF SUMMARY OF THE INVENTION

Embodiments of the present invention address the above needs and achieve other advantages by providing an inspection system capable of acquiring NDI data, as well as associated positional data in order to provide information about the location and characteristics of a flaw within the structure. The system generally includes a robot having a moveable arm, and a non-destructive inspection sensor carried by the moveable arm. The non-destructive inspection sensor is capable of acquiring the data indicative of the structure at approximately the same time associated positional data is acquired so that a flaw may be accurately located. In addition, the system is capable of acquiring the positional data independently of data or other positional information provided by the motion control program that drives the moveable arm, which allows the positional data to be recorded in accordance with a predetermined clock cycle.

In one embodiment of the present invention, a system for inspecting a structure is provided. The system includes at least one non-destructive inspection sensor (e.g., ultrasonic sensor) capable of acquiring data indicative of at least a portion of the structure, as well as at least one positional sensor for acquiring positional data of the non-destructive inspection sensor. The system also includes a mechanism operable to trigger the non-destructive inspection sensor and/or positional sensor to acquire data such that data indicative of the structure and the positional data are acquired at approximately the same time. The system further includes a movable arm carrying the sensors and movably, typically pivotally, attached to a base, wherein the movable arm comprises at least one movable joint between the base and the non-destructive inspection sensor. The system includes a data acquisition system capable of communicating with the sensors such that the data acquisition system generates information indicative of at least a portion of the structure based on data acquired by the each of the sensors.

In various aspects of the present invention, the data acquisition system is capable of generating a three-dimensional point cloud of the structure. The point cloud could include information for detecting a defect in the structure. The data acquisition system is capable of acquiring the positional data at a frequency of at least 200 Hz, for example.

The positional and non-destructive inspection sensors could be moved automatically along the structure. The positional sensor is also capable of providing three-dimensional positional data. The movable arm may include a plurality of movable joints between the base and the non-destructive inspection sensor. A plurality of positional sensors could be co-located at respective movable joints for acquiring positional data.

In another aspect of the present invention, a system for inspecting a structure is provided. The system includes at least one sensor for providing positional data (e.g., three-dimensional positional data). The system also includes a movable arm carrying the sensor and movably attached to a base, wherein the moveable arm includes at least one movable joint. In one embodiment of the present invention, the sensor is a positional encoder located proximate to the movable joint. In addition, the system includes a controller for controlling the motion of the moveable arm, wherein the controller is operable to move the moveable arm in accordance with a predefined motion control program. The sensor is capable of acquiring positional data independent of the motion of the moveable arm. The system could further include a non-destructive inspection sensor for acquiring data indicative of the structure. The system could also include a data acquisition system capable of communicating with each of the sensors such that the data acquisition system generates information indicative of at least a portion of the structure based on the data acquired by the sensors.

Embodiments of the present invention also provide a method for inspecting a structure. The method includes moving a non-destructive inspection sensor proximate to a structure, and triggering the non-destructive inspection sensor and/or at least one positional sensor to acquire data such that data indicative of at least a portion of the structure and associated positional data are acquired at approximately the same time. The method also includes generating information indicative of at least a portion of the structure based on data acquired by the non-destructive inspection sensor and associated positional data.

In various aspects of the present invention, the method includes generating an image (e.g., a three-dimensional point cloud) of the structure based on data acquired by the non-destructive inspection sensor and associated positional data. The moving step could include moving the non-destructive inspection sensor in accordance with a predefined motion control program, wherein the positional sensor is capable of acquiring positional data independent of the motion of the non-destructive sensor. Moreover, the method could include acquiring the positional data at a frequency of at least 200 Hz, for example.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
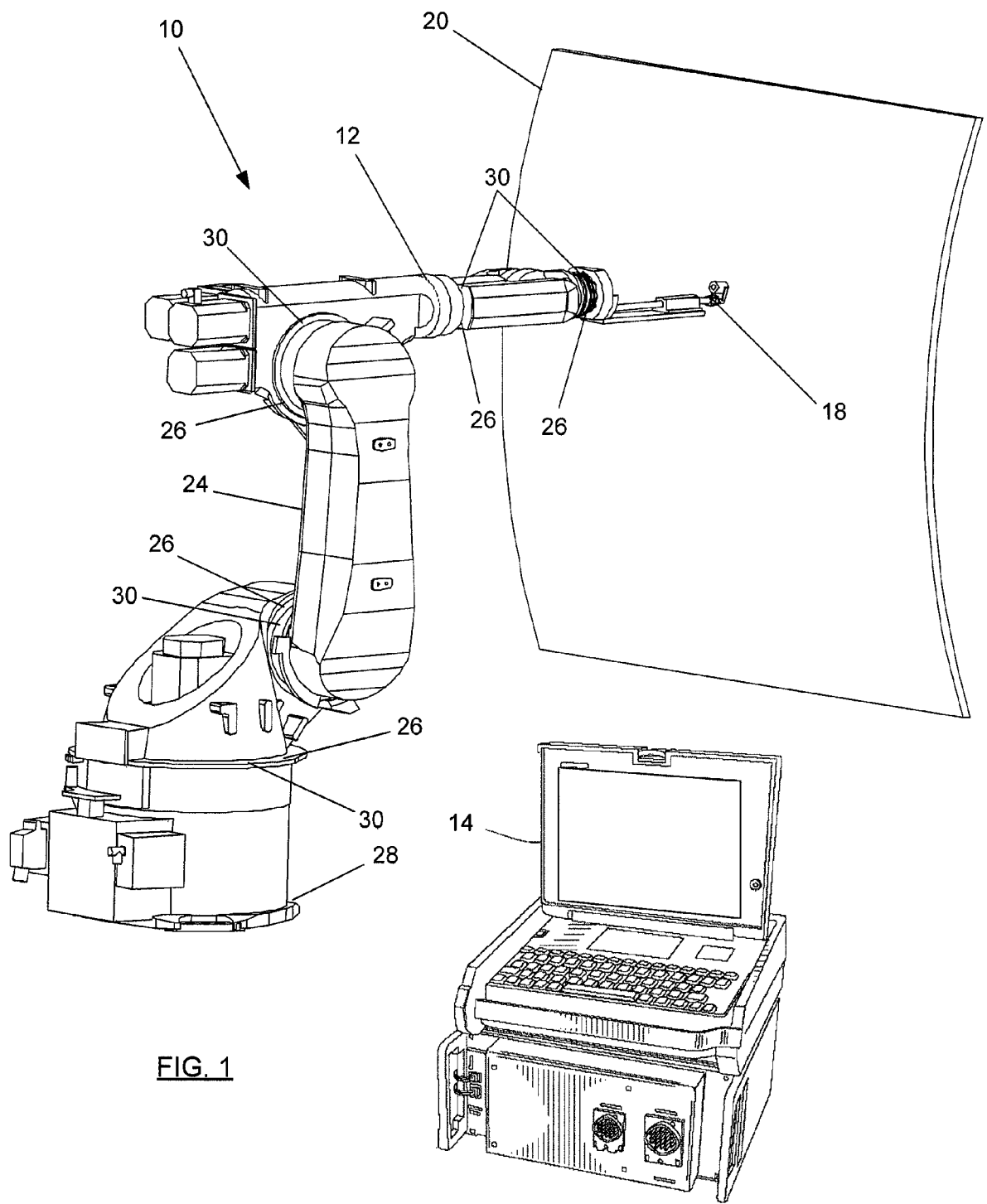
FIG. 1 is a perspective view of an inspection system according to one embodiment of the present invention.
Figure 2:
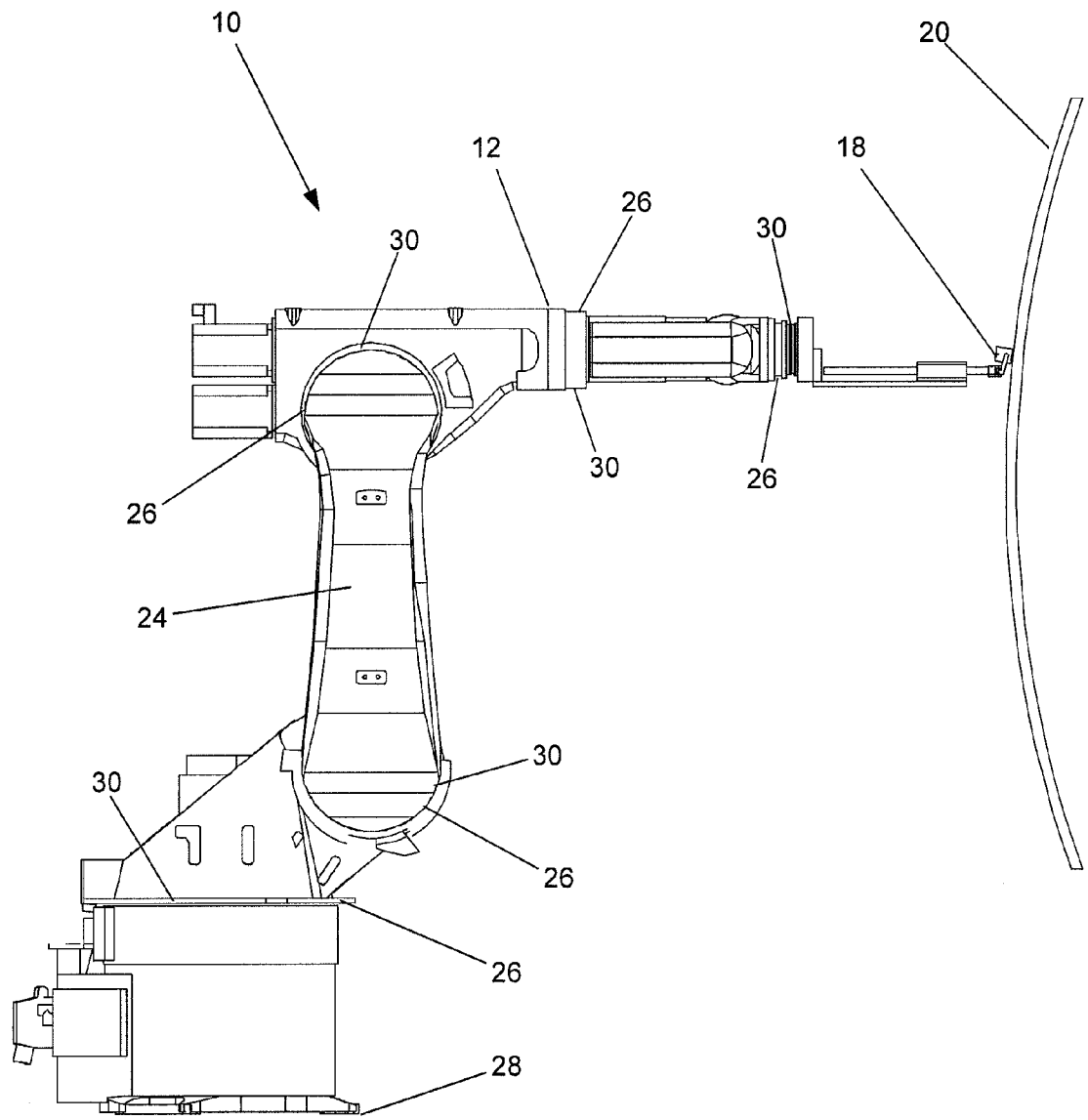
FIG. 2 is an elevation view of the inspection system of FIG. 1.
Figure 3:
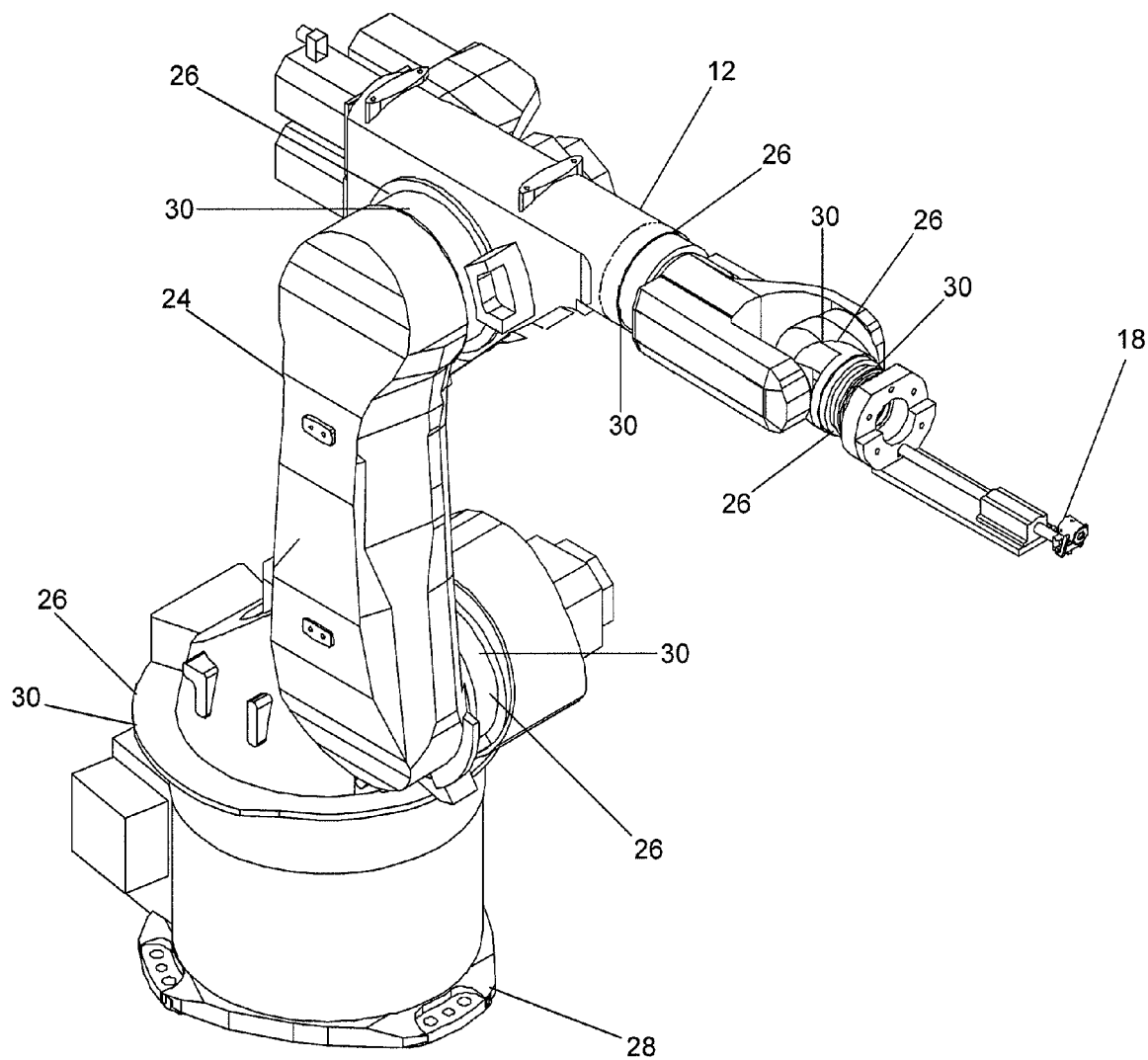
FIG. 3 is a perspective view of a robot carrying a non-destructive sensor according to one embodiment of the present invention.
Figure 4:
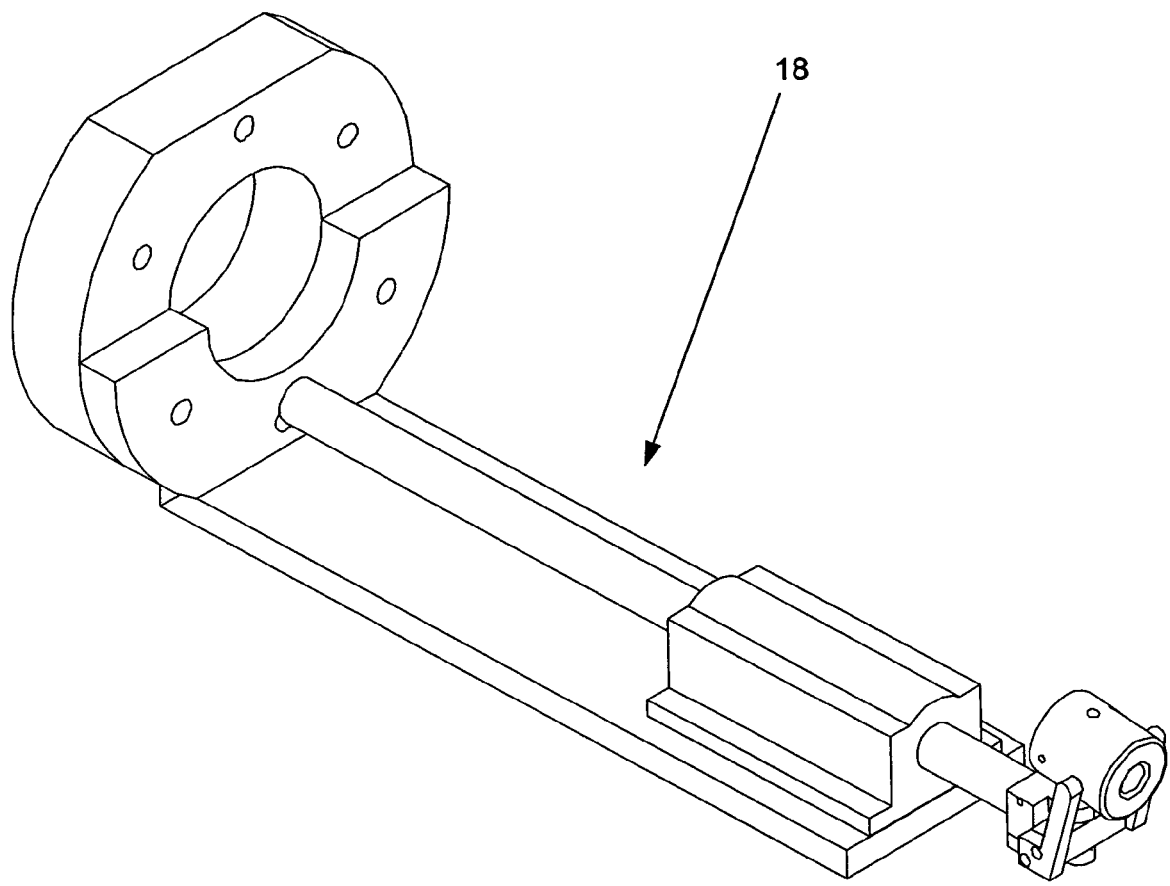
FIG. 4 is a perspective view of a non-destructive sensor according to one embodiment of the present invention.

Referring now to the drawings and, in particular to FIGS. 1-2, there is shown an inspection system 10. The inspection system 10 includes a sensor 18 that is carried by a robot 12 and in communication with a data acquisition system 14. As the sensor 18 is moved along a structure 20, data is sent to the data acquisition system 14 for processing.

Typically, the robot 12 is automatically controlled to move the sensor 18 proximate to the structure 20, while the data acquisition system 14 generates images of the surface of the structure to map the sensor's response.

The inspection system 10 could be used to inspect any number of structures in a variety of industries where detection of flaws or defects in the structure is required, such as in the aircraft, automotive, or construction industries. The sensor 18 is capable of detecting any number of flaws within or along the surface of the structure, such as cracks, disbonds, discontinuities, voids, or porosity, which could adversely affect the performance of the structure.

The term "structure" is not meant to be limiting, as the inspection system 10 could be used to inspect any number of parts or structures of different shapes and sizes, such as machined forgings, castings, or composite panels or parts. The inspection could be performed on newly manufactured structures or existing structures that are being inspected for preventative maintenance purposes. Further, the structure could be any number of materials. For example, the structure could be a metallic material, such as aluminum, or a composite material, such as graphite-epoxy.

Robots, such as that shown in FIG. 1, have typically been developed for producing three-dimensional profiles of structures 20. The robot generally includes multiple-axis movement capabilities and uses software support to generate the three-dimensional profile to be used for measurement and inspection of parts. In particular, the robot 12 shown in FIG. 1 includes a moveable arm 24 having one or more movable connections, hereinafter referenced as pivots 26, although other movable connections are permitted, and a base 28. Therefore, the combination of the moveable arm 24 and pivots 26 provides several degrees of freedom, which in turn, allows the sensor 18 to move in any number of locations and directions. The robot 12 includes one or more positional sensors 30 at, or otherwise associated with, each of the pivots 26 that provide positional data (X, Y, and Z in three-dimensional space) to the data acquisition system 14 for accurately locating the sensor 18. For example, the robot 12 shown in FIG. 1 includes six pivots 26, where each pivot includes a positional encoder 30 that collectively defines the three-dimensional location of the sensor 18. As described below, the sensor 18 provides non-destructive inspection ("NDI") data indicative of the structure 20. As such, the robot 12 provides an accurate location of any defects using positional data and NDI data acquired during inspection of the structure 20.

The robot 12 could be differently sized depending on the type of structure 20 inspected, and is generally easily manipulated so that the sensor 18 is moved along the structure with minimal effort. The robot 12 could be permanently fixed or portable so that it may be used at different locations or within a lab, and may even be used remotely to conveniently inspect structures 20 onsite to reduce the amount of downtime typically required to transport the structure to a central inspection location. An example of a robot 12 that could be employed with the present invention is manufactured by the Kuka Roboter GmbH (Augsburg, Germany), although any robot or coordinate measurement machine capable of carrying a sensor 18 and communicating with a data acquisition system 14 could be used. Furthermore, the robot 12 could include various numbers of sensors 30 (e.g., one or more) for acquiring positional data, and the sensors 30 could be located at different locations, such as proximate to sensor 18.

The data acquisition system 14 is capable of generating various images, including A-scan, B-scan, and C-scan images of complex shaped structures 20 based on data collected by the positional sensors 30 and sensor 18. Furthermore, the data acquisition system 14 is capable of generating a three-dimensional point cloud based on the data acquired by the positional sensors 30 and sensor 18. Thus, a stream of positional data may be mapped to a stream of NDI data to generate the point cloud. The NDI data may include, among other information, data regarding defects, irregularities, or other imperfections in the structure 20.

The data acquisition system 14 typically includes a processor or similar computing device operating under the control of imaging software so that any defects in the structure 20 may be presented on a display. The processor could be embodied by a computer such as a desktop, laptop, or portable processing device capable of processing the data generated by the positional sensors 30 and sensor 18 and creating an image of the scanned data that is shown on a display such as a monitor or other viewing device. The data acquisition system 14 generates images of the data and also allows a user to store and edit previously created images. Therefore, a permanent record of the images may be kept for future use or record keeping. However, it is understood that the data acquisition system 14 need not generate images, as the data acquisition system could mathematically collect and analyze positional and NDI data that a technician could use to characterize and locate a flaw based on the data.

The sensor 18 could be any suitable sensor or probe capable of generating information for inspecting a structure 20, and could be attached to the robot 12 using any suitable technique, such as with various fasteners. The sensor 18 is typically a non-destructive sensor, such that the sensor is capable of inspecting a structure 20 without harming the structure or requiring disassembly of the structure. In the embodiment of the inspection system 10 shown in FIG. 1, the sensor 18 is an ultrasonic sensor. The ultrasonic sensor 18 could be a surface-riding or thin-filmed probe, as known to those skilled in the art. However, the sensor 18 could be various types of NDI sensors, such as pulse-echo, thru-transmission, shear wave, resonance, pitch/catch, mechanical impedance, or ultrasonic array sensors. Typically, there would be a sensor 18 for collecting NDI data and one or more sensors 30 or encoders for collecting positional data. However, in one variation of the present invention, there could be a single sensor 18 capable of collecting NDI data and associated positional data. Similarly, there may be more than one sensor 18 for acquiring NDI data, such as a sensor array, if necessary.

In one embodiment, the inspection system 12 also includes a trigger, such as a transistor-transistor-logic ("TTL") trigger, as known to those skilled in the art, that is utilized to trigger the sensor 18 to acquire NDI data. In particular, the TTL sensor triggers the sensor 18 to acquire NDI data at the same time, or substantially the same time, that one or more sensors 30 are acquiring positional data. As a result, the NDI data and positional data are correlative and capable of providing a precise three-dimensional location of the NDI data. The TTL trigger would typically be used by an independent buffered data acquisition system, which could be available via a network.

In one embodiment, one or more sensors 30 associated with the robot 12 are capable of acquiring positional data at a predetermined frequency, in other words, in accordance with a predetermined clock cycle. The positional sensors 30 are typically capable of acquiring positional data at a frequency of at least 200 Hz. In other words, if the robot 12 moves the sensor 18 at a speed of approximately 20 inches per second, the positional sensors 30 of this embodiment acquire positional data about every 0.1 inch. In addition, using the TTL trigger, the sensor 18 is capable of acquiring NDI data at approximately the same frequency and at approximately the same time that positional data is acquired. It is understood that the sensors 30 could acquire data at various frequencies, for example, frequencies as high as 500 Hz or higher may be achieved with the inspection system 10. Conventional inspection systems are capable of acquiring positional data at about 10 Hz such that the inspection system 10 of some embodiments of the present invention is able to acquire more data and over-sample the structure 20. Over-sampling allows the inspection system 10 to generate more data than would typically be required such that a higher resolution of an image may be achieved.

The inspection system 10 also includes a servo controller for controlling the motion of the moveable arm 24. The controller is operable to move the moveable arm 24 independently of the positional data acquired by the positional sensors 30. Consequently, the positional sensors 30 are capable of acquiring positional data in accordance with a predetermined clock cycle, which is unlike conventional inspection systems where the controller typically gives priority to controlling the motion of the robot 12. Therefore, the frequency with which the positional sensors 30 acquire positional data is typically unaffected by the motion of the robot 12, and the positional sensors 30 are able to acquire a greater amount of positional data at a constant frequency and in real time without concern regarding motion of the robot. Generally, the robot 12 motion is programmed independently of the data acquisition process by the positional sensors 30 so that the position feedback of the positional sensors 30 is the only data that need be relied upon for determining the location of the sensor 18. In other words, the location of the sensor 18 is determined from the data acquired by the positional sensors 30 without reliance upon any data or other information that could be provided by the robot's 12 motion control program. However, it is understood that the motion of the robot 12 need not be programmed independently of the data acquisition process for acquiring positional data. For example, there may be instances where the frequency at which the positional sensors 30 are required to acquire positional data is not imperative.

The robot 12 is typically in communication with the data acquisition system 14 to process the data accumulated by the positional sensors 30 and sensor 18 and to display the processed data. In many cases, communications cable(s) transmit data between the robot 12 and the data acquisition system 14. In other embodiments, the data may be transmitted between the robot 12 and the data acquisition system 14 via wireless communications. The robot 12 may be directly connected to the processor, or indirectly connected, such as via a network. In further embodiments of the present invention the data acquisition system 14 may be located proximate to the robot 12, such that remote connections between the robot and data acquisition system are not necessary. Moreover, it is understood that data acquisition system 14 could be incorporated with the robot 12 such that the data is collected and processed by the robot.

FIGS. 1 and 2 demonstrate that the sensor 18 can be moved automatically along a curved structure 20 to inspect for flaws. Thus, the robot 12 may pivot or rotate the moveable arm 24 about pivots 26 to move the sensor 18 in various directions and positions along the structure 20. As shown in FIG. 1, the data acquisition system 14 includes a display capable of illustrating an image, as described earlier. Further, the sensor 18 is generally capable of moving over a smooth, relatively rough, complex, and/or contoured surface while maintaining the desired orientation and proximity with the structure 20, such as perpendicular to the structure.

Thus, embodiments of the present invention are capable of using off-the-shelf, high-speed robots in conjunction with NDI technology. As such the inspection system 10 can gather greater amounts of data at increased speeds. Acquiring the three-dimensional position with the positional sensors 30 and NDI data with sensor 18 provides greater detail for characterizing a flaw within the structure 20. Utilizing a trigger, such as a TTL trigger, also ensures that the NDI data is acquired at about the same time that the positional data is acquired so that the NDI and positional data are properly correlated. Moreover, positional data may be captured by the positional sensors 30 in a manner that is independent of data or other information that may be provided by the robot's 12 motion control program, which allows the positional sensors 30 to acquire positional data in a consistent clock cycle and in real time. The data acquisition system 14 is also capable of generating three-dimensional images that increase the probability of detecting and locating a defect in the structure 20. In addition, the robot 12 provides several degrees of freedom, which allows the sensor 18 to be adapted for inspecting structures 20 having complex shapes. Furthermore, the inspection system 10 is accurate so that defects are conveniently depicted and located for repair and/or replacement of the structure 20.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A system for inspecting a structure comprising:
at least one non-destructive inspection sensor for acquiring data indicative of the structure;
at least one positional sensor for acquiring positional data of the non-destructive inspection sensor;
a mechanism operable to trigger at least one of the non-destructive inspection sensor and the positional sensor to acquire data such that data indicative of the structure and the positional data are acquired at approximately the same time;
a movable arm carrying each of the sensors and being movably attached to a base, wherein the movable arm comprises at least one movable joint between the base and the non-destructive inspection sensor;
a data acquisition system capable of communicating with each of the sensors such that the data acquisition system generates information indicative of at least a portion of the structure based on the data acquired by each of the sensors; and
a controller for controlling the motion of the moveable arm, wherein the controller is operable to move the movable arm in accordance with a predefined motion control program, wherein the at least one positional sensor is capable of acquiring positional data independent of the motion of the movable arm, and wherein the controller is operable to move the movable arm independent of the positional data acquired by the at least one positional sensor.

2. The system according to claim 1, wherein the data acquisition system is capable of generating a three-dimensional point cloud of the structure.

3. The system according to claim 2, wherein the point cloud comprises information for detecting a defect in the structure.

4. The system according to claim 1, wherein the non-destructive inspection sensor is an ultrasonic sensor.

5. The system according to claim 1, wherein the movable arm comprises a plurality of movable joints between the base and the non-destructive inspection sensor.

6. The system according to claim 5, wherein a plurality of positional sensors are co-located at respective movable joints for acquiring positional data.

7. The system according to claim 1, wherein the positional sensor is capable of providing three-dimensional positional data.

8. The system according to claim 1, wherein each of the positional sensor and non-destructive inspection sensor is moved automatically along the structure.

9. The system according to claim 1, wherein the data acquisition system is capable of acquiring the positional data at a frequency of at least 200 Hz.

10. The system according to claim 1, wherein the at least one positional sensor is a positional encoder located proximate to a joint.

11. A method for inspecting a structure comprising:
moving a non-destructive inspection sensor proximate to a structure in accordance with a predefined motion control program;
triggering at least one of the non-destructive inspection sensor and at least one positional sensor to acquire data such that data indicative of at least a portion of the structure and associated positional data are acquired at approximately the same time, wherein the at least one positional sensor is capable of acquiring positional data independent of the motion of the non-destructive inspection sensor, and wherein the motion of the non-destructive inspection sensor is independent of positional data acquired by the positional sensors; and
generating information indicative of at least a portion of the structure based on data acquired by the non-destructive inspection sensor and associated positional data.

12. The method according to claim 11, wherein generating comprises generating an image of the structure based on data acquired by the non-destructive inspection sensor and associated positional data.

13. The method according to claim 11, wherein generating comprises generating a three-dimensional point cloud of the structure.

14. The method according to claim 11, further comprising acquiring the positional data at a frequency of at least 200 Hz.

15. The method according to claim 11, wherein moving comprises moving the non-destructive inspection sensor automatically.

* * * * *